United States Patent [19]

Gironda

[11] Patent Number: 5,534,487
[45] Date of Patent: Jul. 9, 1996

[54] STABILIZATION OF 3-ISOTHIAZOLONE SOLUTIONS

[75] Inventor: Kevin F. Gironda, Alpha, N.J.

[73] Assignee: Rohm and Haas Company, Philadelphia, Pa.

[21] Appl. No.: 441,913

[22] Filed: May 16, 1995

[51] Int. Cl.$^6$ .................... A01N 43/80; C07D 275/03
[52] U.S. Cl. .................... 504/290; 514/372; 548/213; 252/8.57; 252/404; 510/119; 510/237; 510/382; 510/383; 510/518; 508/271
[58] Field of Search .................... 514/372; 504/290; 548/213

[56] References Cited

U.S. PATENT DOCUMENTS

| | | | |
|---|---|---|---|
| Re. 34,185 | 2/1993 | Amick | 548/213 |
| 4,906,274 | 3/1990 | Mattox | 71/67 |
| 5,373,016 | 12/1994 | Brown et al. | 514/372 |
| 5,376,677 | 12/1994 | Trah | 514/443 |
| 5,424,324 | 6/1995 | Willingham | 514/372 |

*Primary Examiner*—Johann Richter
*Assistant Examiner*—Laura R. Cross
*Attorney, Agent, or Firm*—Michael B. Fein

[57] ABSTRACT

The present invention provides a method of stabilizing solutions of 3-isothiazolone compounds using a stabilizing compound of the formula:

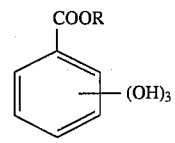

wherein R is $C_1$–$C_6$ alkyl; and compositions which comprise 3-isothiazolone compound, solvent and stabilizing compound.

10 Claims, No Drawings

STABILIZATION OF 3-ISOTHIAZOLONE SOLUTIONS

This invention relates to the stabilization of solutions of 3-isothiazolones.

Certain 3-isothiazolone compounds are well known microbicides. Among these are mixtures of 5-chloro-2-methyl-3-isothiazolone (or 5-chloro-2-methyl-4-isothiazolin- 3-one or "CMI") and 2-methyl-3-isothiazolone (or 2-methyl-4-isothiazolin- 3-one or "MI"), and 2-n-octyl-3-isothiazolone (or 2-n-octyl-4-isothiazolin- 3-one or "OI"). These compounds are inherently unstable and commercial products require the addition of a stabilizer.

The most prevalent stabilizer for mixtures of CMI and MI is magnesium nitrate. Typical 14% concentrates of mixtures of CMI and MI are stabilized with 16% magnesium nitrate, while typical dilute solutions (0.5 to 5% in water) of CMI and MI are stabilized either with 23% magnesium nitrate or magnesium nitrate with additional copper salt stabilizers. These high levels of stabilization salts often cause problems in certain loci, such as shock in latexes.

One solution to this problem is to use an organic stabilizer. U.S. Pat. No. 4,906,274 discloses orthoesters as stabilizers for 3-isothiazolone compounds. While these stabilizers work well for organic systems, the orthoesters hydrolyze when used in an aqueous system, thereby losing their stabilizing effect. U.S. Pat. No. RE 34,185 discloses the use of hydroxylic solvents as stabilizers. These stabilizers also work well, but again lose their stabilizing effect when used in an aqueous system.

U.S. Pat. No. 5,373,016 to Brown, et al. discloses that certain known free-radical scavengers stabilize 3-isothiazolones against decomposition by free-radicals. Free radicals are molecular fragments which have at least one unpaired electron, which cause the free-radicals to seek one electron in a reaction. Free radicals behave differently from nucleophiles, which are ions or molecules that have an electron-rich center. Such an electron-rich center enables the nucleophiles to donate a pair of electrons to form a bond. Among the free-radical scavengers disclosed by Brown is propyl gallate.

U.S. patent application Ser. No. 07/601,964 discloses a number of carbonyl containing compounds as stabilizers for 3-isothiazolones. Among these stabilizers are $C_7$–$C_{10}$ aromatic acids.

I have discovered an alternate approach to stabilizing solutions of one or more 3-isothiazolone compounds against decomposition by nucleophiles without using metal salts by providing a method of stabilizing 3-isothiazolone compounds comprising introducing to said 3-isothiazolone compound in a solvent and 0.1 to 5% by weight of a stabilizing compound of the formula:

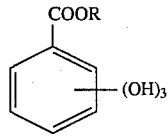

wherein R is $C_1$–$C_6$ alkyl.

Typical nucleophiles which can decompose 3-isothiazolones include, for example, hydroxide salts, such as sodium hydroxide, potassium hydroxide, and the like; thiols; amines; and the like.

The 3-isothiazolone compounds to which this invention is most applicable are CMI, MI, and OI, either alone or in admixture. The invention is especially applicable to CMI and MI, either alone or in admixture. When in admixture, the preferred ratio of CMI to MI is from 90:10 to 2:98 and especially preferred is a ratio of 3:1 to 4:1. Another mixture to which this invention is especially suitable for use in certain loci, such as latex or paint, comprises MI and OI.

Suitable stabilizers include, for example, methyl gallate (or methyl 3,4,5-trihydroxybenzoate), ethyl gallate (or ethyl 3,4,5-trihydroxybenzoate), and propyl gallate (or propyl 3,4,5-trihydroxybenzoate). The actual amount of stabilizer used depends on the concentration of 3-isothiazolone compound.

Solvents are used to dissolve the 3-isothiazolone compounds. Such solvents may be water; a water miscible organic solvent which dissolves the 3-isothiazolone, is compatible with the proposed end use, does not destabilize the 3-isothiazolone, dissolves the stabilizer and does not react with the stabilizer to eliminate its stabilizing action; or mixtures of water and a water miscible organic solvent. Suitable water miscible organic solvents are glycols, such as ethylene glycol, propylene glycol, diethylene glycol and dipropylene glycol. Water and water/glycol mixtures are preferred.

The compositions of the invention are useful as biocides and comprise from 0.5 to 5% by weight of one or more 3-isothiazolone compounds, solvent, and 0.1 to 5% by weight of stabilizer.

Preferred compositions comprise from 1 to 2% by weight of one or more 3-isothiazolone compounds and from 0.5 to 1.5% by weight of stabilizer.

The compositions of the invention are prepared by mixing the 3-isothiazolone compound, stabilizer, and solvent in any order.

The term microbicide includes bactericides, fungicides, and algaecides. Microbicidal or biocidal activity is intended to include both the inhibition of growth of and elimination of microbial organisms, such as bacteria, fungi, and algae.

Uses of these stabilized microbicides are typically at arty locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, these stabilized microbicides may also be used in all applications for which known microbicidal compositions are useful; preferred utilities of the compositions of the invention are to protect wood; latex; adhesive; glue; paper; textile; leather; plastics; cardboard; caulking; feed; cosmetics, e.g. shampoos, conditioners, lotions, and creams; and household products, e.g. dish detergents, floor waxes, cleaning products, and the like.

Because isothiazolones are so active as microbicides and only low levels of stabilizer are required to achieve stabilization, the amount of stabilizer in systems being treated will be very low, and therefore it is not likely to interfere with other components in systems requiring protection or with systems to which protected systems will be applied.

It is known in the art that the performance of microbicides may be enhanced by combination with one or more other microbicides. Thus, other known microbicides may be combined advantageously with the composition of this invention.

The least stable of the aforementioned 3-isothiazolone compounds is CMI, and testing for stability of that compound is most relevant. In most cases, compositions according to this invention comprising CMI are stable enough that no more than 40% of CMI is degraded after 3 weeks storage at 55° C.

3

The 3-isothiazolones used in the examples were an approximate 3:1 mixture of CMI and MI. All percentages are by weight. Samples were analyzed for the percentage of CMI remaining by HPLC with UV detection. Samples having at least 60% CMI remaining after 3 weeks storage at 55° C. are considered stable.

EXAMPLE 1

To each of two 30 ml glass, screw cap vials were added 8.0 g of dipropylene glycol, 1.75 g of deionized water and 0.16 g of 3-isothiazolones (1.5%). To one of these samples (Sample 1-1) were added 0.10 g (1%) of propyl gallate as stabilizer. Sample 1-2 contained no added stabilizer. Both samples were capped, shaken and stored at 55° C. The samples were analyzed after 1, 2, 3, and 4 weeks storage. The results are as follows:

| Sample | Stabilizer | % CMI Remaining | | | |
|---|---|---|---|---|---|
| | | 1 Week | 2 Weeks | 3 Weeks | 4 Weeks |
| 1-1 | Propyl gallate | 98 | 98 | 96 | 49 |
| 1-2# | None | 100 | 97 | 41 | 0 |

# = Comparative

These data clearly show that propyl gallate stabilizes the 3-isothiazolones.

EXAMPLE 2 (COMPARATIVE)

This example demonstrates the superior stabilizing ability of propyl gallate ("PG") in nucleophilic systems over the prior art free-radical stabilizer 3,3-thiodipropionic acid ("TDP") of U.S. Pat. No. 5,373,016. Both 1,2-benzisothiazolin-3-one ("BIT") and an approximate 3:1 mixture of CMI and MI were subjected to stability tests in free-radical and nulceophilic systems. Ammonium persulfate ("APS") was used as the free-radical, as described in U.S. Pat. No. 5,373,016, and ethanolamine was used as the nucleophile. When BIT was added to a sample, it was added in an amount of 33 μl of a 30% aqueous solution. When CMI/MI were added to a sample, they were added in an amount of 70 μl of a 1.4% aqueous solution.

Six samples, labeled 2-1 to 2-6, were prepared in 30 ml glass, screw cap vials. To each vial were added 10 ml of deionized water and 0.014 g (1428 ppm) APS. To Samples 2-3 to 2-6 were further added either TDP or PG in the amounts shown in Table 4-1 and either BIT or CMI/MI, in the amounts described above. Once the samples were prepared, they were capped, shaken and stored in an oven at 60° C. for one hour. After this time, the samples were removed from the oven and analyzed for % BIT or CMI remaining. These results are reported in Table 4-1.

TABLE 4-1

| Sample | TDP (ppm) | PG (ppm) | % BIT Remaining | % CMI Remaining |
|---|---|---|---|---|
| 2-1 | 0 | 0 | 40 | — |
| 2-2 | 0 | 0 | — | 92 |
| 2-3 | 0.011 g (1114 ppm) | 0 | 61 | — |
| 2-4 | 0.011 g (1114 ppm) | 0 | — | 100 |
| 2-5 | 0 | 0.014 g (1405 ppm) | 57 | — |
| 2-6 | 0 | 0.014 g | — | 100 |

4

TABLE 4-1-continued

| Sample | TDP (ppm) | PG (ppm) | % BIT Remaining | % CMI Remaining |
|---|---|---|---|---|
| | | (1405 ppm) | | |

From these data it can be seen that CMI is stable in free-radical systems and the addition of either TDP or PG do not significantly enhance CMI stability. These data further show that BIT does significantly decompose in the presence of free-radicals.

Six samples, labeled 2-7 to 2-12, were prepared in 30 ml glass, screw cap vials. To each vial were added 10 ml of deionized water and 0.007 g (696 ppm) ethanolamine. To Samples 2-9 to 2-12 were further added either TDP or PG in the amounts shown in Table 4-2 and either BIT or CMI/MI, in the amounts described above. Once the samples were prepared, they were capped, shaken and stored in an oven at 60° C. for one hour. After this time, the samples were removed from the oven and analyzed for % BIT or CMI remaining. These results are reported in Table 4-2.

TABLE 4-2

| Sample | TDP (ppm) | PG (ppm) | % BIT Remaining | % CMI Remaining |
|---|---|---|---|---|
| 2-7 | 0 | 0 | 100 | — |
| 2-8 | 0 | 0 | — | 63 |
| 2-9 | 0.011 g (1114 ppm) | 0 | 100 | — |
| 2-10 | 0.011 g (1114 ppm) | 0 | — | 71 |
| 2-11 | 0 | 0.014 g (1405 ppm) | 92 | — |
| 2-12 | 0 | 0.014 g (1405 ppm) | — | 86 |

These data clearly show that CMI is decomposed by nucleophiles, losing 37% in one hour, whereas BIT is stable to nucleophiles without the need for added stabilizer. These data further show that propyl gallate is a surprisingly better stabilizer for CMI in nucleophilic systems than TDP.

EXAMPLE 3 (COMPARATIVE)

The stabilizing ability of gallic acid (3,4,5-trihydroxybenzoic acid, a $C_7$ aromatic acid) was compared to methyl gallate and propyl gallate. To each of three 30 ml glass, screw cap vials were added 8.0 g of dipropylene glycol, 1.75 g deionized water, 0.16 g 3-isothiazolones (1.6%), and 0.10 g stabilizer (1%). The vials were capped, stored at 55 ° C., and analyzed after 1, 2, and 3 weeks. The data are reported below.

| Sample | Stabilizer | % CMI Remaining | | |
|---|---|---|---|---|
| | | 1 Week | 2 Weeks | 3 Weeks |
| 3-1# | gallic acid | 100 | 97 | 30 |
| 3-2 | methyl gallate | 100 | 98 | 63 |
| 3-3 | propyl gallate | 100 | 94 | 70 |

# = Comparative

From these data it can be seen that the esters of gallic acid, methyl gallate and propyl gallate, are surprisingly more effective stabilizers for 3-isothiazolones than gallic acid itself.

What is claimed is:

1. A composition useful as a biocide comprising 0.5 to 5% 3-isothiazolone compound(s) selected from the group consisting of 5-chloro-2-methyl-3-isothiazolone, 2-methyl-3-isothiazolone, and 2-n-octyl-3-isothiazolone, solvent comprising water, a nucleophile, and a sufficient amount of a stabilizing compound of the formula:

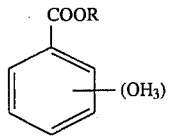

to stabilize said 3-isothiazolone against said nucleophile, said sufficient amount being 0.1 to 5 parts of said stabilizing compound per 0.5 to 5 parts of said 3-isothiazolone compound(s).

2. The composition according to claim 1 wherein said 3-isothiazolone compound comprises 1 to 2% by weight.

3. The composition according to claim 1 wherein said solvent is water; a water miscible organic solvent selected front the group consisting of ethylene glycol, propylene glycol, diethylene glycol, and dipropylene glycol; or a mixture of water and said water miscible organic solvent.

4. The composition according to claim 1 wherein said stabilizing compound is selected from the group consisting of methyl gallate, ethyl gallate, and propyl gallate.

5. The composition according to claim 1 wherein said 3-isothiazolone is a mixture of 5-chloro-2-methyl-3-isothiazolone and 2-methyl-3-isothiazolone, said solvent is water, and said stabilizing compound is propyl gallate.

6. A method of stabilizing 3-isothiazolone compound(s) selected from the group consisting of 5-chloro-2-methyl-3-isothiazolone, 2-methyl-3-isothiazolone, and 2-n-octyl-3-isothiazolone against decomposition by nucleophiles without using metal salts comprising introducing to said 3-isothiazolone compound(s) a solvent and a sufficient amount of a stabilizing compound of the formula:

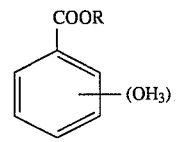

to stabilize said 3-isothiazolone against said nucleophile, said sufficient amount being 0.1 to 5 parts per 0.5 to 5 parts of said 3-isothiazolone.

7. The method according to claim 6 wherein said solvent is water; a water miscible organic solvent selected from the group consisting of ethylene glycol, propylene glycol, diethylene glycol, and dipropylene glycol; or a mixture of water and said water miscible organic solvent.

8. The method according to claim 6 wherein said stabilizing compound is selected from the group consisting of methyl gallate, ethyl gallate, and propyl gallate.

9. The method according to claim 6 wherein said 3-isothiazolone is a mixture of 5-chloro-2-methyl-3-isothiazolone and 2-methyl-3-isothiazolone, said aqueous solvent is water, and said stabilizing compound is propyl gallate.

10. A method of use of protecting a locus against microbicidal attack comprising introducing on, at, or into said locus a sufficient amount of a composition according to claim 1, said locus being selected from the group consisting of cooling water systems, laundry rinse water, cutting oils, lubricants, oil fields, wood, latex, adhesive, glue, paper, textile, leather, plastics, cardboard, caulking, feed, cosmetics, shampoos, conditioners, lotions, creams, dish detergents, floor waxes, and cleaning compositions.

* * * * *